United States Patent
Peters et al.

(10) Patent No.: US 7,994,156 B2
(45) Date of Patent: Aug. 9, 2011

(54) CARBOXYLIC ACID 4-PHENYLAZO-PHENYL ESTER DERIVATIVES AND THEIR USE AS MONOAMINE NEUROTRANSMITTER RE-UPTAKE INHIBITORS

(75) Inventors: Dan Peters, Malmö (SE); John Paul Redrobe, Rødovre (DK); βlsebet Østergaard Nielsen, København K (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/745,530

(22) PCT Filed: Nov. 27, 2008

(86) PCT No.: PCT/EP2008/066296
§ 371 (c)(1), (2), (4) Date: Aug. 13, 2010

(87) PCT Pub. No.: WO2009/068595
PCT Pub. Date: Jun. 4, 2009

(65) Prior Publication Data
US 2010/0311699 A1    Dec. 9, 2010

(30) Foreign Application Priority Data
Nov. 30, 2007  (DK) ................................ 2007 01715

(51) Int. Cl.
| | |
|---|---|
| *C07D 487/08* | (2006.01) |
| *C07D 295/205* | (2006.01) |
| *C07D 471/08* | (2006.01) |
| *C07D 243/08* | (2006.01) |
| *A61K 31/551* | (2006.01) |
| *A61K 31/4353* | (2006.01) |
| *A61K 31/4985* | (2006.01) |
| *A61P 25/00* | (2006.01) |

(52) U.S. Cl. .................... 514/150; 534/752; 534/798
(58) Field of Classification Search .................. None
See application file for complete search history.

(56) References Cited

U.S. PATENT DOCUMENTS

| | | | |
|---|---|---|---|
| 7,662,808 B2* | 2/2010 | Peters et al. | 514/183 |
| 7,687,523 B2* | 3/2010 | Peters et al. | 514/338 |
| 7,750,011 B2* | 7/2010 | Peters et al. | 514/252.02 |
| 2008/0146582 A1* | 6/2008 | Peters et al. | 514/252.04 |
| 2009/0075983 A1* | 3/2009 | Peters et al. | 514/221 |
| 2010/0234384 A1* | 9/2010 | Peters et al. | 514/249 |

FOREIGN PATENT DOCUMENTS

| | | |
|---|---|---|
| WO | WO 2007/093600 A1 | 8/2007 |
| WO | WO 2007/135120 A1 | 11/2007 |
| WO | WO 2007/135122 A1 | 11/2007 |

OTHER PUBLICATIONS

Cuckle, Howard S., "Primary Prevention of Down's syndrome", International Journal of Medical Sciences, 2005.*

* cited by examiner

*Primary Examiner* — Fiona T Powers
(74) *Attorney, Agent, or Firm* — Birch, Stewart, Kolasch & Birch, LLP

(57) ABSTRACT

This invention relates to novel carboxylic acid 4-phenylazo-phenyl ester derivatives useful as monoamine neurotransmitter re-uptake inhibitors.

In other aspects the invention relates to the use of these compounds in a method for therapy and to pharmaceutical compositions comprising the compounds of the invention.

13 Claims, No Drawings

CARBOXYLIC ACID 4-PHENYLAZO-PHENYL ESTER DERIVATIVES AND THEIR USE AS MONOAMINE NEUROTRANSMITTER RE-UPTAKE INHIBITORS

This application is the National Phase of PCT/EP2008/066296 filed on Nov. 27, 2008, which claims priority under 35 U.S.C. 119(e) to U.S. Provisional Application No. 60/991,875 filed on Dec. 3, 2007, and under 35 U.S.C. 119(a) to Patent Application No. PA 2007 01715 filed in Denmark on Nov. 30, 2007, all of which are hereby expressly incorporated by reference into the present application.

TECHNICAL FIELD

This invention relates to novel carboxylic acid 4-phenylazo-phenyl ester derivatives useful as monoamine neurotransmitter re-uptake inhibitors.

In other aspects the invention relates to the use of these compounds in a method for therapy and to pharmaceutical compositions comprising the compounds of the invention.

BACKGROUND ART

Serotonin Selective Reuptake Inhibitors (SSRIs) currently provide efficacy in the treatment of several CNS disorders, including depression and panic disorder. SSRIs are generally perceived by psychiatrists and primary care physicians as effective, well-tolerated and easily administered. However, they are associated with a number of undesirable features.

Thus, there is still a strong need for compounds with an optimised pharmacological profile as regards the activity on reuptake of the monoamine neurotransmitters serotonin, dopamine and noradrenaline, such as the ratio of the serotonin reuptake versus the noradrenaline and dopamine reuptake activity.

SUMMARY OF THE INVENTION

It is an object of the invention to provide novel compounds which show activity as monoamine neurotransmitter re-uptake inhibitors.

A further object of the invention is the provision of compounds which optionally—in addition to the re-uptake inhibitor activity—show activity as modulators of the nicotinic acetylcholine receptors, in particular the nicotinic acetylcholine α7 receptor, and in particular activity as nicotinic acetylcholine α7 receptor subtype agonists.

In its first aspect, the invention provides a compound of Formula I:

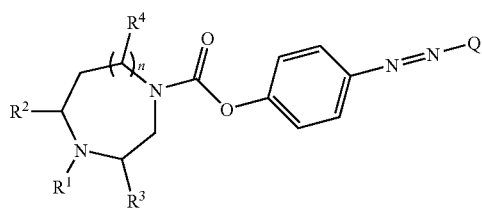

any of its stereoisomers or any mixture of its stereoisomers, or a pharmaceutically acceptable salt thereof; wherein $R^1$, $R^2$, $R^3$, $R^4$, n and Q are as defined below.

In its second aspect, the invention provides a pharmaceutical composition, comprising a therapeutically effective amount of a compound of the invention, any of its stereoisomers or any mixture of its stereoisomers, or a pharmaceutically acceptable salt thereof, together with at least one pharmaceutically acceptable carrier, excipient or diluent.

In a further aspect, the invention provides the use of a compound of the invention, any of its stereoisomers or any mixture of its stereoisomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In a still further aspect, the invention relates to a method for treatment, prevention or alleviation of a disease or a disorder or a condition of a living animal body, including a human, which disorder, disease or condition is responsive to responsive to inhibition of monoamine neurotransmitter re-uptake in the central nervous system, which method comprises the step of administering to such a living animal body in need thereof a therapeutically effective amount of a compound of the invention, any of its stereoisomers or any mixture of its stereoisomers, or a pharmaceutically acceptable salt thereof.

Other objects of the invention will be apparent to the person skilled in the art from the following detailed description and examples.

DETAILED DISCLOSURE OF THE INVENTION

Carboxylic Acid 4-phenylazo-phenyl Ester Derivatives

In its first aspect the present invention provides compounds of Formula I:

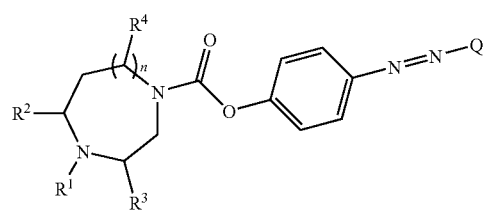

any of its stereoisomers or any mixture of its stereoisomers, or a pharmaceutically acceptable salt thereof,
wherein
Q represents a phenyl group;
  which phenyl group is optionally substituted with one or more substituents independently selected from the group consisting of:
    halo, trifluoromethyl, trifluoromethoxy, cyano and alkoxy;
n is 0 or 1;
$R^1$ represents hydrogen or alkyl; and
either $R^2$ and $R^3$ together form —CH$_2$—CH$_2$—, —CH$_2$—CH$_2$—CH$_2$— or —CH$_2$—CH$_2$—CH$_2$—CH$_2$—; and $R^4$ represents hydrogen;
or $R^1$ and $R^4$ together form —CH$_2$—CH$_2$—; and $R^3$ represents hydrogen;
or $R^2$, $R^3$ and $R^4$ each represent hydrogen.

In one embodiment of the compound of formula I, n is 1; $R^1$ and $R^4$ together form —$CH_2$—$CH_2$—; and $R^3$ represents hydrogen.

In a second embodiment, n is 0; and $R^2$ and $R^3$ together form —$CH_2$—$CH_2$—.

In a further embodiment, n is 0; and $R^2$ and $R^3$ together form —$CH_2$—$CH_2$—$CH_2$—.

In a still further embodiment, n is 0; and $R^2$ and $R^3$ together form —$CH_2$—$CH_2$—$CH_2$—$CH_2$—.

In a further embodiment, n is 1; $R^2$ and $R^3$ together form —$CH_2$—$CH_2$—; and $R^4$ represents hydrogen.

In a still further embodiment, n is 1; $R^2$ and $R^3$ together form —$CH_2$—$CH_2$—$CH_2$—; and $R^4$ represents hydrogen.

In a further embodiment, n is 0; and $R^2$ and $R^3$ each represent hydrogen.

In a still further embodiment, n is 1; and $R^2$ and $R^3$ each represent hydrogen.

In a further embodiment, $R^1$ represents alkyl. In a special embodiment, $R^1$ represents methyl.

In a still further embodiment, Q represents phenyl.

In a special embodiment, the compound of the invention is 1,4-Diaza-bicyclo[3.2.2]nonane-4-carboxylic acid 4-phenylazo-phenyl ester;

9-Methyl-3,9-diaza-bicyclo[3.3.1]nonane-3-carboxylic acid 4-phenylazo-phenyl ester;

4-Methyl-piperazine-1-carboxylic acid 4-phenylazo-phenyl ester;

4-Methyl-[1,4]diazepane-1-carboxylic acid 4-phenylazo-phenyl ester;

8-Methyl-3,8-diaza-bicyclo[3.2.1]octane-3-carboxylic acid 4-phenylazo-phenyl ester;

10-Methyl-8,10-diaza-bicyclo[4.3.1]decane-8-carboxylic acid 4-phenylazo-phenyl ester;

10-Methyl-3,10-diaza-bicyclo[4.3.1]decane-3-carboxylic acid 4-phenylazo-phenyl ester;

9-Methyl-3,9-diaza-bicyclo[4.2.1]nonane-3-carboxylic acid 4-phenylazo-phenyl ester;

or a pharmaceutically acceptable salt thereof.

Any combination of two or more of the embodiments as described above is considered within the scope of the present invention.

Definition Of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Alkoxy is O-alkyl, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers or cis-trans-isomers.

The invention includes all such stereoisomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L- (tartrates, mandelates, or camphorsulphonate) salts for example.

The chemical compounds of the present invention may also be resolved by the formation of diastereomeric amides by reaction of the chemical compounds of the present invention with an optically active carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to inhibit reuptake of the monoamines dopamine, noradrenaline and serotonin in synaptosomes e.g. such as described in WO 97/30997 (NeuroSearch A/S). Based on the balanced activity observed in these tests the compound of the invention is considered useful for the treatment, prevention or alleviation of a disease or a disorder or a condition of a mammal, including a human, which disease, disorder or condition is responsive to inhibition of monoamine neurotransmitter re-uptake in the central nervous system.

In a special embodiment, the compounds of the invention are considered useful for the treatment, prevention or alleviation of: mood disorder, depression, atypical depression, depression secondary to pain, major depressive disorder, dysthymic disorder, bipolar disorder, bipolar I disorder, bipolar II disorder, cyclothymic disorder, mood disorder due to a general medical condition, substance-induced mood disorder, pseudodementia, Ganser's syndrome, obsessive compulsive disorder, panic disorder, panic disorder without agoraphobia, panic disorder with agoraphobia, agoraphobia without history of panic disorder, panic attack, memory deficits, memory loss, attention deficit hyperactivity disorder, obesity, anxiety, generalized anxiety disorder, eating disorder, Parkinson's disease, parkinsonism, dementia, dementia of ageing, senile dementia, Alzheimer's disease, Down's syndrome, acquired immunodeficiency syndrome dementia complex, memory dysfunction in ageing, specific phobia, social phobia, social anxiety disorder, post-traumatic stress disorder, acute stress disorder, chronic stress disorder, drug addiction, drug abuse, drug abuse liability, cocaine abuse, nicotine abuse, tobacco abuse, alcohol addiction, alcoholism, kleptomania, withdrawal symptoms caused by termination of use of addictive substances, pain, chronic pain, inflammatory pain, neuropathic pain, diabetic neuropathic pain, migraine pain, tension-type headache, chronic tension-type headache, pain associated with depression, fibromyalgia, arthritis, osteoarthritis, rheumatoid arthritis, back pain, cancer pain, irritable bowel pain, irritable bowel syndrome, post-operative pain, post-mastectomy pain syndrome (PMPS), post-stroke pain, drug-induced neuropathy, diabetic neuropathy, sympathetically-maintained pain, trigeminal neuralgia, dental pain, myofacial pain, phantom-limb pain, bulimia, premenstrual syndrome, premenstrual dysphoric disorder, late luteal phase syndrome, post-traumatic syndrome, chronic fatigue syndrome, persistent vegetative state, urinary incontinence, stress incontinence, urge incontinence, nocturnal incontinence, sexual dysfunction, premature ejaculation, erectile difficulty, erectile dysfunction, premature female orgasm, restless leg syndrome, periodic limb movement disorder, eating disorders, anorexia nervosa, sleep disorders, pervasive developmental disorders, autism, Asperger's disorder, Rett's disorder, childhood disintegrative disorder, learning disabilities, motor skills disorders, mutism, trichotillomania, narcolepsy, post-stroke depression, stroke-induced brain damage, stroke-induced neuronal damage, Gilles de la Tourettes disease, tinnitus, tic disorders, body dysmorphic disorders, oppositional defiant disorder or post-stroke disabilities. In a preferred embodiment, the compounds are considered useful for the treatment, prevention or alleviation of depression.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Nicotinic Acetylcholine Receptor Activity

Compounds of the invention may be tested for their ability to bind to the nicotinic acetylcholine α7 receptor as described in WO 2006/087306 (NeuroSearch A/S).

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of monoamine neurotransmitter re-uptake in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosage regimen may be reduced.

EXAMPLES

The invention is further illustrated with reference to the following examples, which are not intended to be in any way limiting to the scope of the invention as claimed.

Preparatory Examples

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane (Intermediate compound)

The title compound was prepared according to *J. Med. Chem.* 1993 36 2311-2320 (and according to the slightly modified method described below).

1,4-Diazabicyclo[3.2.2]nonane (Intermediate compound)

To the solution of 1,4-diazabicyclo[3.2.2]nonan-3-one (15.8 g; 113 mmol) in absolute dioxane (130 ml) LiAlH$_4$ (4.9 g; 130 mmol) was added under argon. The mixture was refluxed for 6 hours and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate compound)

To the solution of 3-quinuclidinone hydrochloride (45 g; 278 mmol) in 90 ml of water hydroxylamine hydrochloride (21 g; 302 mmol) and sodium acetate (CH$_3$COOHx3H$_2$O; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid (190 g). The temperature of the solution during the reaction was kept at 130° C. After addition of all oxime the solution was stirred for 20 minutes at the same temperature, then transferred to an enameled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

1,4-Diaza-bicyclo[3.2.2]nonane-4-carboxylic acid 4-phenylazo-phenyl ester fumaric acid salt A mixture of 4-phenylazophenol (1.0 g, 5.04 g), pyridine (0.52 g, 6.6 mmol) and dichloromethane (40 ml) was added dropwise to a mixture of phosgene in toluene (12.5 g, 25.2 mmol) and dichloromethane (25 ml) at 0° C. and was stirred for 1 h at the same temperature. The mixture was stirred at room-temperature for 15 h. The mixture was evaporated and co-evaporated with toluene. The formed 4-phenylazo-phenylchloroformate was solved in DME (50 ml), followed by addition of 1,4-diazabicyclo[3.2.2]nonane (0.64 g, 5.04 mmol) at room-temperature, followed by stirring over-night at room temperature. Aqueous sodium hydroxide (1 M) was added, DME was evaporated and the mixture was extracted with chloroform. Chromatography on silica gel with chloroform, 10% methanol and 1% aqueous ammonia as solvent gave a crude product. Yield 1.68 g (95%). The corresponding salt was obtained by addition of a diethyl ether and methanol mixture (9:1) saturated with fumaric acid. Yield 1.39 g (62%). LC-ESI-HRMS of [M+H]+ shows 351.1827 Da. Calc. 351.182101 Da, dev. 1.7 ppm.

9-Methyl-3,9-diaza-bicyclo[3.3.1]nonane-3-carboxylic acid 4-phenylazophenyl ester fumaric acid salt Was prepared according to method A from 9-methyl-3,9-diazabicyclo[3.3.1]nonane and 4-phenylazophenol. LC-ESI-HRMS of [M+H]+ shows 365.1984 Da. Calc. 365.197751 Da, dev. 1.8 ppm 4-Methyl-piperazine-1-carboxylic acid 4-phenylazo-phenyl ester free base Was prepared according to method A from 1-methylpiperazine and 4-phenylazophenol. LC-ESI-HRMS of [M+H]+ shows 325.1678 Da. Calc. 325.166451 Da, dev. 4.1 ppm.

4-Methyl-[1,4]diazepane-1-carboxylic acid 4-phenylazo-phenyl ester fumaric acid salt Was prepared according to method A from 1-methyl-[1,4] diazepane and 4-phenylazophenol. LC-ESI-HRMS of [M+H]+ shows 339.1804 Da. Calc. 339.182101 Da, dev. −5 ppm.

8-Methyl-3,8-diaza-bicyclo[3.2.1]octane-3-carboxylic acid 4-phenylazo-phenyl ester free base Was prepared according to method A from 8-methyl-3,8-diazabicyclo[3.2.1]octane and 4-phenylazophenol. LC-ESI-HRMS of [M+H]+ shows 351.1813 Da. Calc. 351.182101 Da, dev. −2.3 ppm.

10-Methyl-8,10-diaza-bicyclo[4.3.1]decane-8-carboxylic acid 4-phenylazophenyl ester fumaric acid salt Was prepared according to method A from 10-methyl-8, 10-diaza-bicyclo[4.3.1]decane and 4-phenylazophenol. LC-ESI-HRMS of [M+H]+ shows 379.2144 Da. Calc. 379.213401 Da, dev. 2.6 ppm.

10-Methyl-3,10-diaza-bicyclo[4.3.1]decane-3-carboxylic acid 4-phenylazophenyl ester fumaric acid salt Was prepared according to method A from 10-methyl-3, 10-diaza-bicyclo[4.3.1]Decane and 4-phenylazophenol. LC-ESI-HRMS of [M+H]+ shows 379.2119 Da. Calc. 379.213401 Da, dev. −4 ppm.

9-Methyl-3,9-diaza-bicyclo[4.2.1]nonane-3-carboxylic acid 4-phenylazophenyl ester fumaric acid salt Was prepared according to method A from 9-methyl-3,9-diaza-bicyclo[4.2.1]nonane and 4-phenylazophenol. LC-ESI-HRMS of [M+H]+ shows 365.1989 Da. Calc. 365.197751 Da, dev. 3.1 ppm.

Biological Data

In Vitro Inhibition Activity

A compound of the invention was tested for its ability to inhibit the reuptake of the monoamine neurotransmitters dopamine (DA) noradrenaline (NA) and serotonine (5-HT) in synaptosomes as described in WO 97/16451.

The test values are given as $IC_{50}$ (the concentration (μM) of the test substance which inhibits the specific binding of $^3$H-DA, $^3$H-NA, or $^3$H-5-HT by 50%).

Test results obtained by testing the compound of the present invention appear from the below table:

TABLE 1

| Test compound | 5-HT-uptake $IC_{50}$ (μM) | DA-uptake $IC_{50}$ (μM) | NA-uptake $IC_{50}$ (μM) |
|---|---|---|---|
| 1,4-Diaza-bicyclo[3.2.2]nonane-4-carboxylic acid 4-phenylazo-phenyl ester | 13 | 0.032 | 0.018 |

In Vitro Inhibition of $^3$H-α-Bungarotoxin Binding in Rat Brain

In this example the affinity of the compound of the invention for binding to $α_7$-subtype of nicotinic receptors is determined.

α-Bungarotoxin is a peptide isolated from the venom of the Elapidae snake *Bungarus multicinctus*. It has high affinity for neuronal and neuromuscular nicotinic receptors, where it acts as a potent antagonist. $^3$H-α-Bungarotoxin labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes.

The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 µl of homogenate are added to 25 µl of test solution and 25 µl of $^3$H-α-bungarotoxin (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 2 below.

TABLE 2

Inhibition of $^3$H-α-Bungarotoxin Binding

| Compound | $IC_{50}$ (µM) |
|---|---|
| 1,4-Diaza-bicyclo[3.2.2]nonane-4-carboxylic acid 4-phenylazo-phenyl ester | 1.6 |

The invention claimed is:

1. A compound of Formula I:

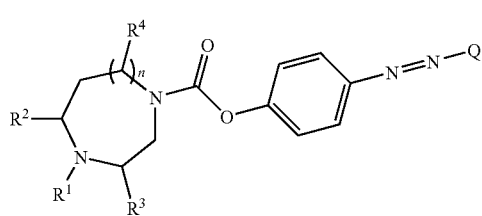

(I)

any of its stereoisomers or any mixture of its stereoisomers, or a pharmaceutically acceptable salt thereof, wherein
Q represents a phenyl group;
  which phenyl group is optionally substituted with one or more substituents independently selected from the group consisting of:
    halo, trifluoromethyl, trifluoromethoxy, cyano and alkoxy;
n is 0 or 1;
$R^1$ represents hydrogen or alkyl; and
either $R^2$ and $R^3$ together form —CH$_2$—CH$_2$—, —CH$_2$—CH$_2$—CH$_2$— or —CH$_2$—CH$_2$—CH$_2$—CH$_2$—; and $R^4$ represents hydrogen;
or $R^1$ and $R^4$ together form —CH$_2$—CH$_2$—; and $R^3$ represents hydrogen;
or $R^2$, $R^3$ and $R^4$ each represent hydrogen.

2. The compound according to claim 1, any of its stereoisomers or any mixture of its stereoisomers, or a pharmaceutically acceptable salt thereof, wherein
n is 1;
$R^1$ and $R^4$ together form —CH$_2$—CH$_2$—; and
$R^3$ represents hydrogen.

3. The compound according to claim 1, any of its stereoisomers or any mixture of its stereoisomers, or a pharmaceutically acceptable salt thereof, wherein
n is 0; and
$R^2$ and $R^3$ together form —CH$_2$—CH$_2$—.

4. The compound according to claim 1, any of its stereoisomers or any mixture of its stereoisomers, or a pharmaceutically acceptable salt thereof, wherein
n is 0; and
$R^2$ and $R^3$ together form —CH$_2$—CH$_2$—CH$_2$—.

5. The compound according to claim 1, any of its stereoisomers or any mixture of its stereoisomers, or a pharmaceutically acceptable salt thereof, wherein
n is 0; and
$R^2$ and $R^3$ together form —CH$_2$—CH$_2$—CH$_2$—CH$_2$—.

6. The compound according to claim 1, any of its stereoisomers or any mixture of its stereoisomers, or a pharmaceutically acceptable salt thereof, wherein
n is 1;
$R^2$ and $R^3$ together form —CH$_2$—CH$_2$—; and
$R^4$ represents hydrogen.

7. The compound according to claim 1, any of its stereoisomers or any mixture of its stereoisomers, or a pharmaceutically acceptable salt thereof, wherein
n is 1;
$R^2$ and $R^3$ together form —CH$_2$—CH$_2$—CH$_2$—; and
$R^4$ represents hydrogen.

8. The compound according to claim 1, any of its stereoisomers or any mixture of its stereoisomers, or a pharmaceutically acceptable salt thereof, wherein
n is 0; and
$R^2$ and $R^3$ each represent hydrogen.

9. The compound according to claim 1, any of its stereoisomers or any mixture of its stereoisomers, or a pharmaceutically acceptable salt thereof, wherein
n is 1; and
$R^2$ and $R^3$ each represent hydrogen.

10. The compound according to claim 1, any of its stereoisomers or any mixture of its stereoisomers, or a pharmaceutically acceptable salt thereof, wherein
$R^1$ represents alkyl.

11. The compound according to claim 1, any of its stereoisomers or any mixture of its stereoisomers, or a pharmaceutically acceptable salt thereof, wherein
Q represents phenyl.

12. The compound according to claim 1, selected from the group consisting of
1,4-Diaza-bicyclo[3.2.2]nonane-4-carboxylic acid 4-phenylazo-phenyl ester;
9-Methyl-3,9-diaza-bicyclo[3.3.1]nonane-3-carboxylic acid 4-phenylazo-phenyl ester;
4-Methyl-piperazine-1-carboxylic acid 4-phenylazo-phenyl ester;
4-Methyl-[1,4]diazepane-1-carboxylic acid 4-phenylazo-phenyl ester;
8-Methyl-3,8-diaza-bicyclo[3.2.1]octane-3-carboxylic acid 4-phenylazo-phenyl ester;
10-Methyl-8,10-diaza-bicyclo[4.3.1]decane-8-carboxylic acid 4-phenylazo-phenyl ester;
10-Methyl-3,10-diaza-bicyclo[4.3.1]decane-3-carboxylic acid 4-phenylazo-phenyl ester;
and
9-Methyl-3,9-diaza-bicyclo[4.2.1]nonane-3-carboxylic acid 4-phenylazo-phenyl ester; or any of its stereoisomers or any mixture of its stereoisomers or a pharmaceutically acceptable salt thereof.

13. A pharmaceutical composition, comprising a therapeutically effective amount of a compound according to claim 1, any of its stereoisomers or any mixture of its stereoisomers, or a pharmaceutically acceptable salt thereof, together with at least one pharmaceutically acceptable carrier, excipient or diluent.

* * * * *